US011930435B2

(12) United States Patent
Fu et al.

(10) Patent No.: US 11,930,435 B2
(45) Date of Patent: *Mar. 12, 2024

(54) DEVICE PAIRING TAKING INTO ACCOUNT AT LEAST ONE CONDITION

(71) Applicant: Ascensia Diabetes Care Holdings AG, Basel (CH)

(72) Inventors: Qiang Fu, Briarcliff Manor, NY (US); Alexander Markovic, Media, PA (US); Joseph R. Anstett, Jr., Oak Ridge, NJ (US); Vladislav Milenkovic, Merion Station, PA (US)

(73) Assignee: Ascensia Diabetes Care Holdings AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/871,395

(22) Filed: Jul. 22, 2022

(65) Prior Publication Data

US 2022/0360960 A1    Nov. 10, 2022

Related U.S. Application Data

(63) Continuation of application No. 16/780,546, filed on Feb. 3, 2020, now Pat. No. 11,399,269, which is a
(Continued)

(51) Int. Cl.
*H04W 4/80* (2018.01)
*A61B 5/00* (2006.01)
(Continued)

(52) U.S. Cl.
CPC ............... *H04W 4/80* (2018.02); *A61B 5/002* (2013.01); *A61B 5/14532* (2013.01);
(Continued)

(58) Field of Classification Search
CPC ....... H04W 4/80; H04W 4/027; H04W 12/08; H04W 4/02; H04W 4/023; H04W 4/20;
(Continued)

(56) References Cited

U.S. PATENT DOCUMENTS 8,792,983 B2 *  7/2014  Von Arx ................ G16H 40/67
                                                            607/32
2012/0019379 A1 *  1/2012  Ben Ayed ............... G06F 21/32
                                                            340/5.82
(Continued)

FOREIGN PATENT DOCUMENTS

JP    2003218840 A    7/2003
JP    2005210458 A    8/2005
(Continued)

OTHER PUBLICATIONS

European Patent Office, Decision to Grant a European Patent Pursuant to Article 97(1) EPC, Application No. 14795759.1, dated Jan. 5, 2023, Munich, Germany.
(Continued)

*Primary Examiner* — Tuan H Nguyen
(74) *Attorney, Agent, or Firm* — Erise IP, P.A.

(57) ABSTRACT

Some embodiments of the present invention include pairing two wireless devices by placing at least one of two devices in a pairing mode; performing at least one pairing motion event with at least one of the wireless devices to satisfy at least one pairing condition; detecting satisfaction of the at least one pairing condition; and pairing the two wireless devices in response to detecting satisfaction of the at least one pairing condition. Numerous other aspects are provided.

20 Claims, 5 Drawing Sheets

Related U.S. Application Data continuation of application No. 16/182,547, filed on Nov. 6, 2018, now Pat. No. 10,582,361, which is a continuation of application No. 15/324,632, filed as application No. PCT/US2014/062472 on Oct. 27, 2014, now Pat. No. 10,142,823.

(60) Provisional application No. 62/021,690, filed on Jul. 7, 2014.

(51) Int. Cl.

| | | |
|---|---|---|
| *A61B 5/145* | (2006.01) | |
| *G06F 3/01* | (2006.01) | |
| *H04L 9/40* | (2022.01) | |
| *H04M 1/72412* | (2021.01) | |
| *H04W 4/02* | (2018.01) | |
| *H04W 4/20* | (2018.01) | |
| *H04W 4/60* | (2018.01) | |
| *H04W 12/08* | (2021.01) | |
| *H04W 48/10* | (2009.01) | |
| *H04W 76/10* | (2018.01) | |
| *H04L 67/51* | (2022.01) | |
| *H04W 4/06* | (2009.01) | |
| *H04W 8/00* | (2009.01) | |
| *H04W 48/16* | (2009.01) | |
| *H04W 74/00* | (2009.01) | |
| *H04W 84/18* | (2009.01) | |

(52) U.S. Cl.
CPC .......... *G06F 3/016* (2013.01); *H04L 63/0869* (2013.01); *H04L 63/0876* (2013.01); *H04L 63/107* (2013.01); *H04M 1/72412* (2021.01); *H04W 4/023* (2013.01); *H04W 4/027* (2013.01); *H04W 4/20* (2013.01); *H04W 4/60* (2018.02); *H04W 12/08* (2013.01); *H04W 48/10* (2013.01); *H04W 76/10* (2018.02); *H04L 67/51* (2022.05); *H04M 2201/18* (2013.01); *H04M 2201/26* (2013.01); *H04M 2250/02* (2013.01); *H04M 2250/22* (2013.01); *H04W 4/06* (2013.01); *H04W 8/005* (2013.01); *H04W 48/16* (2013.01); *H04W 74/002* (2013.01); *H04W 84/18* (2013.01)

(58) Field of Classification Search
CPC ....... H04W 4/60; H04W 48/10; H04W 76/10; A61B 5/14532; A61B 5/002; A61B 5/145; A61B 5/00; H04M 1/72412; H04L 63/0876; H04L 63/107; H04L 63/0869; H04L 9/40; G06F 3/016
See application file for complete search history.

(56) References Cited

U.S. PATENT DOCUMENTS

| | | |
|---|---|---|
| 2014/0149742 A1 | 5/2014 | Yau |
| 2015/0025498 A1* | 1/2015 | Estes .................... A61M 5/158 604/151 |

FOREIGN PATENT DOCUMENTS

| | | |
|---|---|---|
| WO | 2010041366 A1 | 4/2010 |
| WO | 2010061542 A1 | 6/2010 |

OTHER PUBLICATIONS

Japan, Notice of Allowance, Application No. 2020-146642, dated Aug. 1, 2022.
WIPO Application No. PCT/US2014/062472, International Search Report and Written Opinion of the International Searching Authority, dated Mar. 23, 2015.
Mare, Shrirang et al.; ZEBRA: Zero-Effort Bilateral Recurring Authentication; IEEE Symposium on Security & Privacy; https://thawproject.files.wordpress.com/2014/03/mare-zebra1.pdf; pp. 1-16; retrieved on Aug. 25, 2022.
Mayrhofer, Rene et al.; Shake Well Before Use: Intuitive and Secure Pairing of Mobile Devices; IEEE Transactions on Mobile Computing; Jun. 2009; pp. 792-806; vol. 8, No. 6; https://eprints.lancs.ac.uk/id/eprint/42452/1/TMC-2008-07-0279-3.pdf; retrieved on Aug. 25, 2022.

* cited by examiner

DEVICE PAIRING TAKING INTO ACCOUNT AT LEAST ONE CONDITION

RELATED APPLICATIONS

The present application is a continuation of U.S. patent application Ser. No. 16/780,546, filed Feb. 3, 2020, now U.S. Pat. No. 11,399,269, which is a continuation of U.S. patent application Ser. No. 16/182,547, filed Nov. 6, 2018, now U.S. Pat. No. 10,582,361, which is a continuation of U.S. patent application Ser. No. 15/324,632, filed Jan. 6, 2017, now U.S. Pat. No. 10,142,823, which is a § 371 filing of PCT/US2014/062472, filed Oct. 27, 2014, which claims priority to U.S. Provisional Patent Application No. 62/021,690, filed Jul. 7, 2014. The above-referenced applications and patents are hereby incorporated by reference in their entirety.

FIELD

Embodiments of the present invention relate to pairing between wireless electronic devices and, more specifically, to efficiently and securely establishing communication via pairing between such devices.

BACKGROUND

Existing pairing methods for securely establishing communications between two wireless devices (e.g., such as between a cell phone and an automobile audio system or a wireless headset, etc.) typically require a particular sequence of non-intuitive steps and the exchange of up to a six digit key that is selected and/or displayed on one device and entered into the other device. In addition to having the user know the required sequence of steps, means for selecting, displaying and/or entering the key are required. Thus, conventional pair-able devices that might not otherwise require a display or a numeric input device for normal operation (e.g., a loud speaker, a heart rate monitor, etc.) may need to include such extra elements in order to be able to pair for secure, wireless operation. Thus, what are needed are methods and apparatus for improved device pairing.

SUMMARY

In some embodiments, a method of pairing two wireless devices is provided. The method includes placing at least one of two devices in a pairing mode; performing at least one pairing motion event with at least one of the wireless devices to satisfy at least one pairing condition; detecting satisfaction of the at least one pairing condition; and pairing the two wireless devices in response to detecting satisfaction of the at least one pairing condition.

In some other embodiments, a system for pairing two wireless devices is provided. The system includes a first wireless device that includes a programmable smart device that is Bluetooth Low Energy (BLE) enabled; and a second wireless device that is BLE enabled. The second wireless device includes a processor and memory storing second wireless device instructions executable on the processor, wherein the second wireless device instructions when executed are operable to place the second wireless device in a pairing mode. The smart device includes a processor and memory storing smart device instructions executable on the processor, wherein the smart device instructions when executed are operable to: detect performance of at least one pairing motion event, determine if performance of at least one pairing motion event satisfied at least one pairing condition, and pair the two wireless devices in response to determining satisfaction of the at least one pairing condition.

In yet other embodiments, a method of pairing two wireless devices is provided. The method includes executing a pairing application on a smart device that is BLE enabled; placing a second BLE enabled device immediately proximate to the smart device; placing the second device in a pairing mode; instructing a user to move the second device away from the smart device; instructing the user to move the second device toward the smart device in response to detecting that a first pairing condition has been satisfied by a first motion event; and pairing the smart device with the second device in response to detecting that a second pairing condition has been satisfied by a second motion event.

Numerous other aspects are provided in accordance with these and other aspects of the invention. Other features and aspects of the present invention will become more fully apparent from the following detailed description, the appended claims and the accompanying drawings.

DETAILED DESCRIPTION

Embodiments of the present invention provide improved methods and apparatus for securely pairing wireless electronic devices to establish a trusted wireless communications channel between the devices. Instead of exchanging a numeric pairing key, embodiments of the present invention use a pairing motion event to satisfy at least one pairing condition before pairing is permitted.

Various wireless protocols such as Bluetooth® Low Energy (BLE) require a pairing process to establish a communications link. BLE is a radio frequency (RF) communications protocol that operates in the 2.4 GHz industrial, scientific and medical (ISM) radio band. The BLE specification includes profile definitions to support communication between devices such as blood glucose meters (BGMs) and a smartphone or tablet, as well as a proximity profile that allows a proximity monitor (e.g., on a smartphone) to detect whether a proximity reporter (e.g., on a BGM) is within a specified range. Physical proximity can be estimated using the radio receiver's received signal strength indicator (RSSI) value.

Embodiments of the present invention provide a novel pairing process that can be used to securely establish a communications link between two devices without requiring a user to enter a key, nor the devices to include facilities for selecting, displaying and/or entering a key. In some embodiments, pairing is performed by putting the devices in pairing mode, moving the devices apart and then together. Using proximity measurement over time (e.g., using the proximity profile for BLE), a communications link can be established based upon first detecting the close proximity of the two devices, then detecting the increasing distance between the devices to a first threshold (e.g., reduced signal strength), and finally detecting the decreasing distance between the device to a second threshold (e.g., increased signal strength). In some other embodiments, pairing is performed by putting the devices in pairing mode and then tapping the two devices together. The tap can be detected using an accelerometer (e.g., on a smart phone). In yet other embodiments, both discovery and pairing are achieved by tapping one device that is in pairing mode with another device that is in a standby mode. The tap event is used to wake the device in standby mode to enter into pairing mode. With both devices in pairing mode, the pairing based on the tap event then proceeds as above.

In each type of the above embodiments, detection of a pre-defined physical motion event (e.g., a changing proximity pattern/motion sequence or a tap event that satisfies at least one pairing condition) while in pairing mode (or upon waking into pairing mode) serves to replace a conventional numeric key exchange process as the basis for securely establishing communications between the two devices. Note that the establishment of the communications link is considered "secure" because only the two devices concurrently undergoing the pre-defined physical event while in pairing mode can establish the link. Eavesdropper devices are precluded from connecting (e.g., by high jacking the connection) because they do not participate in the pre-defined physical motion event (e.g., the tap event or the pairing motion sequence/proximity pattern). In other words, a non-secure pairing system would allow a link to be established by merely putting the two devices in pairing mode within range of each other. Embodiments of the present invention insure that only the intended devices that satisfy a pairing condition by participating in a pairing motion event can be paired and any eavesdropper devices cannot be paired. Thus, these embodiments provide the user with both the convenience of a simple, intuitive pairing procedure and a sense of security and certainty.

Figure 1:
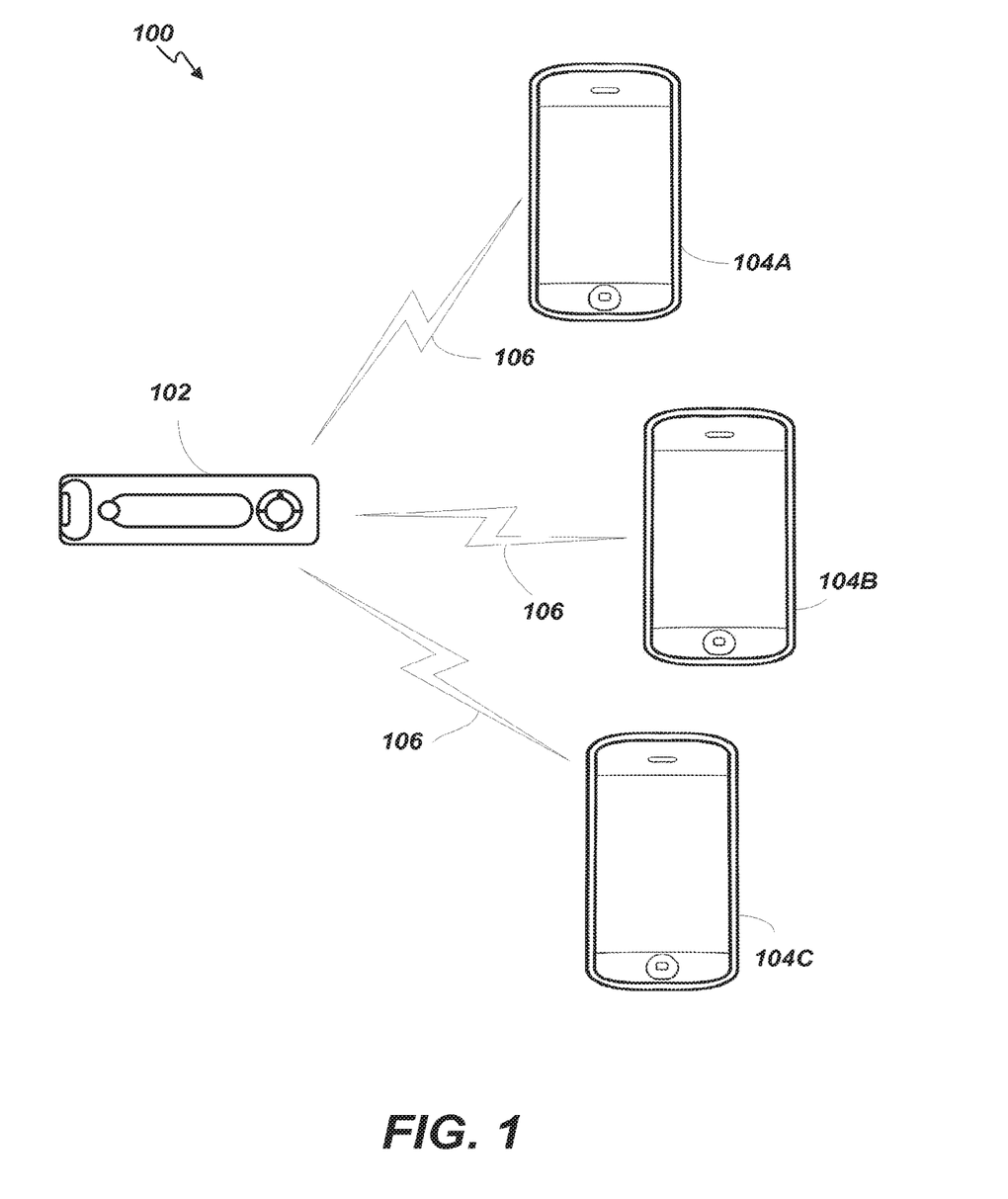
FIG. 1 depicts an example system diagram according to embodiments of the present invention.

Turning to FIG. 1, an example system 100 according to embodiments of the present invention is provided. In some embodiments, the system 100 can include a BGM 102 with BLE capability and one or more smartphones 104A, 104B, 104C also with BLE capability. Note that the example system 100 is shown with a BGM 102 and one or more smartphones 104A, 104B, 104C merely as an illustrative example. Further note that the system 100 can alternatively use any wireless devices that are enabled with any communications protocol (e.g., BLE, Bluetooth, ANT Protocol, etc.) that uses pairing to securely establish a trusted wireless communication link 106. For example, embodiments of the present invention can be used for pairing Bluetooth devices such as the Lockitron Deadbolt, Motorola's H19TXT Headset, the Polaroid Pogo Connect Smart Pen, the Pebble E-Paper Watch, the Wahoo Fitness KICKR stationary exercise bike system, the Nike Hyperdunk+ basketball shoes, the Jabra Solemate docking station speaker system, the Withings Wireless Scale WS-30, the Scosche RHYTHM armband pulse sensor, the Microsoft Sculpt Mobile Keyboard, the Polaroid PoGo Instant Mobile Printer, the Kensington Vo200 Bluetooth Internet Phone, the BlueAnt Supertooth 3 Hands-Free Speakerphone, the Interlink Electronics VP6600 ExpressCard Media Remote for Bluetooth, the Lego Mindstorms NXT Robot Kit, the Baracoda D-Fly Bar Code Scanner, the GARMIN GLO Portable Aviation GPS. In addition, "smart devices" such as smartphones, tablets such as the Apple iPad, any personal or laptop computer with a Bluetooth adapter such as the Kinivo BTD-400 Bluetooth 4.0 USB adapter, any programmable device with wireless communication facility, etc. can be paired using the methods and apparatus of embodiments of the present invention.

Figure 2:
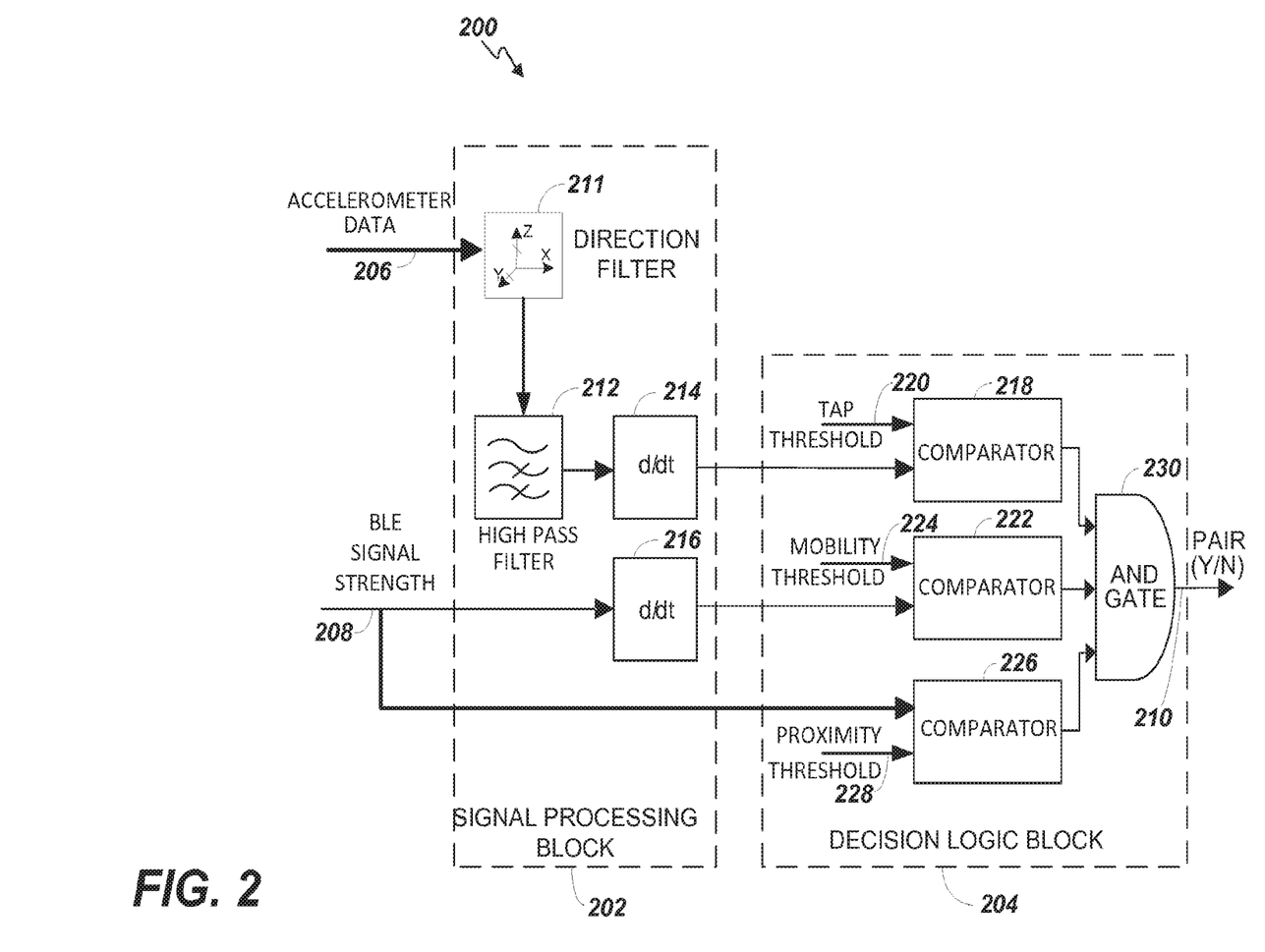
FIG. 2 depicts a functional block diagram of a first example logic circuit according to embodiments of the present invention.

FIG. 2 depicts a functional block diagram illustrating an example logic circuit 200 embodiment of the present invention that uses a tap event for pairing. Note that even though the components of the circuit 200 are represented as hardware devices, in some embodiments, circuit can be embodied as software or a combination of hardware and software components executing on a programmable device (e.g., a smartphone, tablet, etc.). The illustrated embodiment assumes that at least one of the two devices to be paired includes an accelerometer. The example circuit 200, in some embodiments, will only pair the devices if the following three pairing conditions are met. First, the tap is intense enough to yield an accelerometer response above a specified "tap threshold." Second, the RF signal strength is increasing (e.g., devices are getting closer) at a rate above a specified "mobility threshold." Third, the RF signal strength is at a value above a specified "proximity threshold." In some other embodiments, not all three pairing conditions are required to be satisfied for pairing.

In operation, assume that one of the devices to be paired is a BLE enabled smartphone 104A (FIG. 1) that has an accelerometer installed while the other device is a BLE enabled BGM 102. Embodiments of the present invention allow a user to pair the BLE BGM 102 with a smartphone 104A using an installed application and a simple tap to pair procedure. The user starts the application on the smartphone 104A and turns on the BGM 102. The user brings the devices together and taps one against the other. Discovery and pairing will be automatically initiated in response to the sudden change in the accelerometer readings and the proximity of the devices (i.e., a detected change in the BGM 102 BLE signal strength detected by application running on the smartphone 104A).

Thus, embodiments of the invention allow two BLE enabled devices to pair (in terms of the BLE standard) when one device taps another and the pairing conditions are satisfied. As illustrated in the functional block diagram of the logic circuit 200 in FIG. 2, meeting the pairing conditions can be represented as a signal flow gated by the conditions. The example logic circuit 200 is divided into a signal processing block 202 and a decision logic block 204. The signal processing block 202 receives an accelerometer data input signal 206 from the accelerometer and a BLE signal strength signal 208 from the BLE radio receiver. Based on these two input signals and three pre-defined threshold values, the logic circuit 200 creates a binary output signal 210 that indicates whether to pair the devices or not.

The signal processing block 202 determines if sudden changes in acceleration of the smartphone 104A have occurred that indicate a tap event has occurred. In some embodiments, the accelerometer data 206 is initially put through a direction filter 211 to remove components of acceleration in the Y and Z directions. In order to detect the very moment when one device taps another (e.g., instantaneous motion), common "not so sudden" movements (which can be viewed as a low frequency component of the accelerometer data input signal 206) are filtered out from the data generated by the accelerometer. The low frequency component is filtered out by applying a high pass digital filter 212 to the accelerometer data input signal 206. In some embodiments, the high pass digital filter 212 can be embodied as a simple, 1-tap infinite impulse response (IIR) digital filter. This approach also helps to dampen or flatten out effects of gravity on sensor data since the accelerometer measures acceleration associated with the phenomenon of weight experienced by any test mass at rest in the frame of reference of the accelerometer device (e.g., commonly referred to as g-force acceleration).

The physics of a tap event is such that the devices experience some acceleration in the opposite direction (e.g., away from each other) immediately after the tap event. Thus, by taking the derivative of the high pass digital filter 212 output (e.g., the difference between consecutive outputs), the resulting signal is enhanced to show sudden changes in acceleration more clearly. Thus, the signal processing block 202 includes a signal differentiation block 214 that receives the digital filter 212 output and outputs the derivative (i.e., d/dt) of the signal to the decision logic block 204. While in some embodiments this additional signal processing can be optional, enhancing the signal does make the process more robust (e.g., more tolerant of "shake", e.g., from normal jostling) and more reliably able to accurately identify a tap event.

To determine the relative mobility of the devices towards each other (i.e., how quickly the devices are getting closer), the rate of change of the BLE signal strength signal 208 is determined by taking the derivative of the signal 208. Thus, the signal processing block 202 includes a second signal differentiation block 216 that receives the BLE signal strength signal 208 and outputs the derivative (i.e., d/dt) of the signal to the decision logic block 204.

The decision logic block 204 includes a first comparator 218 with inputs coupled to the enhanced signal derived from the high pass digital filter 212 output and a tap threshold value 220 selected to be large enough to insure that the devices were intentionally taped against one another but not so large that the tap could cause damage to either device. The output of the first comparator 218 generates a binary signal that when "TRUE" indicates if the acceleration associated with the tap event was sufficient to exceed the tap threshold value 220.

The decision logic block 204 also includes a second comparator 222 with inputs coupled to the output of the second signal differentiation block 216 and a mobility threshold value 224 selected to be large enough to insure that the devices were intentionally moved together before the tap event. The output of the second comparator 222 generates a binary signal that when "TRUE" indicates if the relative rate of movement of the devices leading up to the tap event was sufficient to exceed the mobility threshold value 224.

The decision logic block 204 also includes a third comparator 226 with inputs coupled to the BLE signal strength signal 208 and a proximity threshold value 228 selected to be large enough to insure that the devices were close enough together at the time of the tap event to insure that they contacted each other. The output of the third comparator 226 generates a binary signal that when "TRUE" indicates that the devices were close enough together (e.g., signal strength indicates proximity) to exceed the proximity threshold value 228.

Coupled to the outputs of the three comparators 218, 222, 226, a logic AND gate 230 receives the binary signals from each. The logic AND gate 230 generates the binary output signal 210 which indicates to pair only if all three binary signals from the three comparators 218, 222, 226 are "TRUE". If any comparator binary output signal is not "TRUE", the logic AND gate 230 generates a signal indicating that the devices should not be paired.

Figure 3:
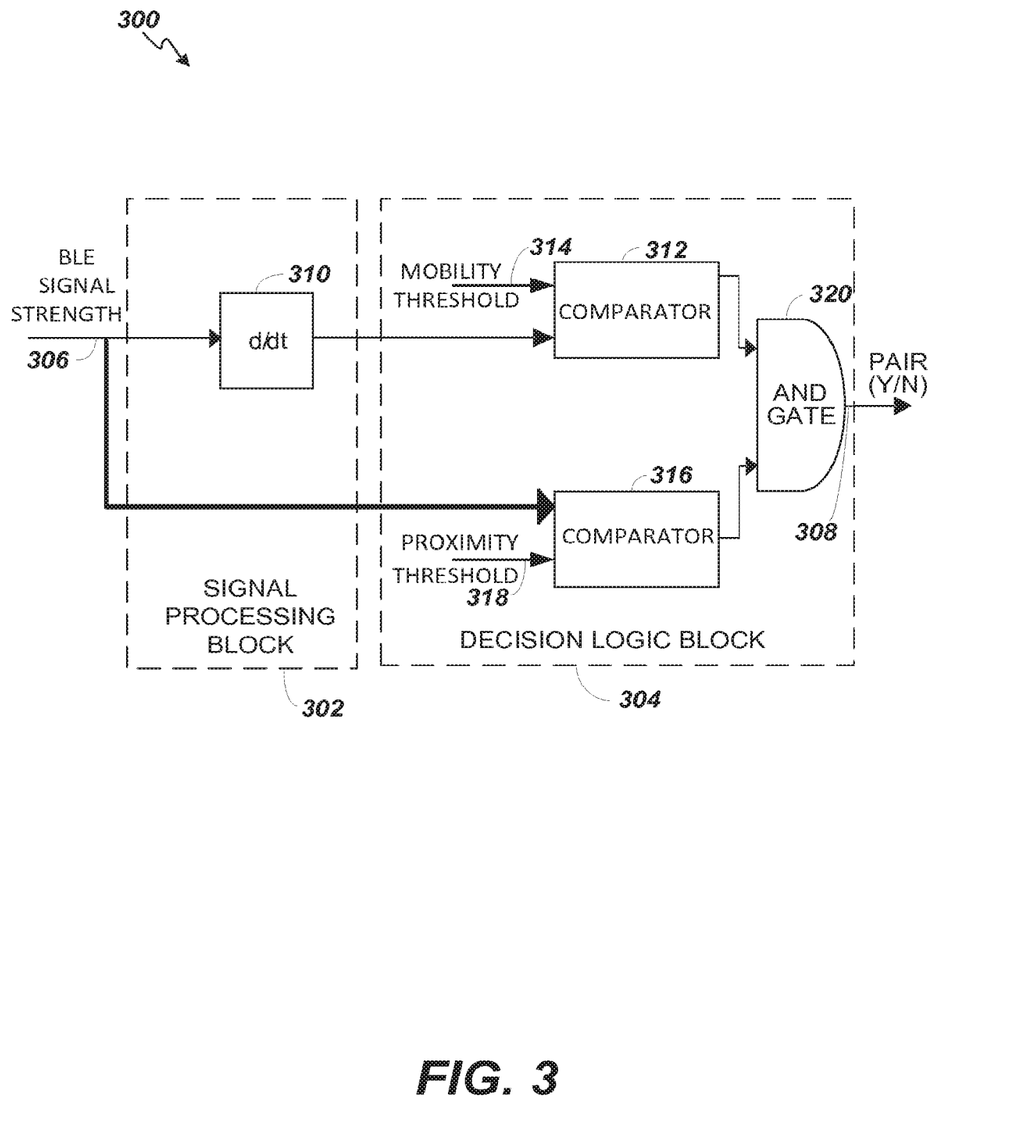
FIG. 3 depicts a logic block diagram of a second example circuit according to embodiments of the present invention.

The above described embodiment uses an accelerometer on the smartphone side to detect a tap event. In embodiments that do not involve a tap event, an accelerometer is not needed. FIG. 3 depicts a logic circuit 300 for a pairing method based on detecting the occurrence of a pre-defined proximity pattern or pairing motion sequence/event instead of a tap event. The pre-defined proximity pattern can be, for example, moving the devices apart to a threshold maximum distance and then moving the devices together to a threshold minimum distance, both movements occurring at a rate above a mobility threshold. Other proximity/motion patterns can be used such as moving the devices together and then apart or moving the devices apart slowly at first and then more rapidly after a certain distance apart is reached.

The logic circuit 300 of FIG. 3 is configured to detect a simple pre-defined proximity pattern or pairing motion sequence/event wherein pairing occurs if the devices start next to each other and are then moved apart at a rate above a mobility threshold. In some embodiments with more complex proximity patterns, the example logic circuit 300 can be used for an initial determination that the devices were moved apart faster than a certain rate and a second logic circuit can be used to determine that a second movement occurred faster than a certain rate. The two movements together can be used to separately satisfy two pairing conditions. Likewise, the logic circuit 300 can be adjusted to detect different pairing motion events at different times to detect a sequence of movements that satisfies corresponding pairing conditions.

The example logic circuit 300 includes a signal processing block 302 and a decision logic block 304. The signal processing block 302 receives a BLE signal strength signal 306 from the BLE radio receiver. Based on this input signal and two threshold values, the logic circuit 300 creates a binary output signal 308 that indicates whether to pair or not.

To determine the relative mobility of the devices towards each other (i.e., how quickly the devices are getting closer), the rate of change of the BLE signal strength signal 306 is determined by taking the derivative of the signal 306. Thus, the signal processing block 302 includes a signal differentiation block 310 that receives the BLE signal strength signal 306 and outputs the derivative (i.e., d/dt) of the signal to the decision logic block 304.

The decision logic block 304 includes a first comparator 312 with inputs coupled to the output of the signal differentiation block 310 and a mobility threshold value 314 selected to be large enough to insure that the devices were moved apart faster than a minimum required rate selected to indicate the movement was intentional. The output of the first comparator 312 generates a binary signal that when "TRUE" indicates if the relative rate of movement apart of the devices was sufficient to exceed the mobility threshold value 314.

The decision logic block 304 also includes a second comparator 316 with inputs coupled to the BLE signal strength signal 306 and a proximity threshold value 318 selected to be large enough to insure that the devices were moved far enough apart to indicate the movement was intentional. The output of the second comparator 316 generates a binary signal that when "TRUE" indicates that the devices were moved far enough apart (e.g., signal strength indicates proximity) to exceed the proximity threshold value 318.

Coupled to the outputs of the two comparators 312, 316, a logic AND gate 320 receives the binary signals from each. The logic AND gate 320 generates the binary output signal 308 which indicates to pair only if both binary signals from the two comparators 312, 316 are "TRUE". If either comparator binary output signal is not "TRUE", the logic AND gate 320 generates a signal 308 indicating that the devices should not be paired.

Figure 4:
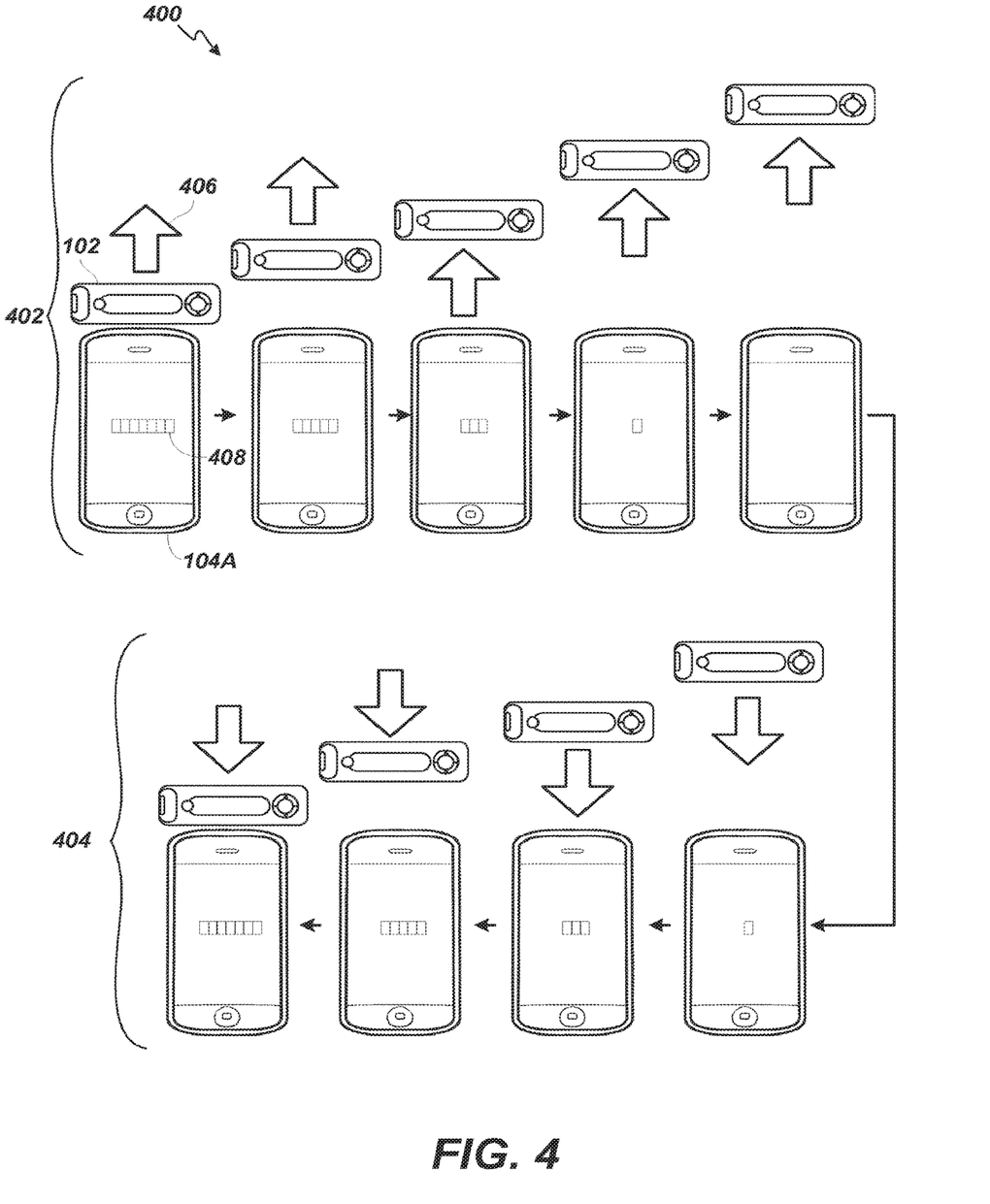
FIG. 4 depicts a pairing motion sequence according to embodiments of the present invention.

Turning now to FIG. 4, an example pairing motion sequence 400 or proximity pattern is illustrated. The pairing motion sequence 400 includes a first motion event 402 where the devices (e.g., a smartphone 104A and a BGM 102), which are initially adjacent each other, are moved apart to at least a pre-defined distance from each other and a second motion event 404 where the devices are moved together. The motion direction arrows 406 (only one labeled) indicated the movement of the BGM 102 away from the smartphone 104A during the first motion event 402 and toward the smartphone 104A during the second motion event 404. Note that the first motion event 402 is broken down into five steps and with each step the BGM 102 is moved a bit further away from the smartphone 104A. Likewise, the second motion event 404 is broken down into four steps and with each step the BGM 102 is moved a bit closer to the smartphone 104A.

Also note that as a reference for a user, an optional segmented proximity indicator bar 408 is displayed on the smartphone 104A. The segmented proximity indicator bar 408 can be part of a user interface adapted to aid a user in executing the pairing motion sequence. The display changes based upon the relative distance between the BGM 102 and the smartphone 104A. The closer the two devices, the more segments of the indicator bar are displayed and the further apart the two devices, the fewer segments of the indicator bar are displayed. Thus, for example, when the user has moved the devices far enough apart to satisfy the pre-defined distance condition of the pairing motion sequence 400, the segmented proximity indicator bar 408 disappears. Likewise, when the pairing motion sequence 400 starts and ends, the segmented proximity indicator bar 408 is displayed with all of the segments.

In some embodiments, alternative displays or graphics can be used to indicate the proximity of the devices to each other. For example, instead of or in addition to a segmented bar, a series of concentric circles can be used. In some embodiments, colors can be used. For example, a color spectrum ranging from red to purple can be used where red indicates the devices are proximate to each other and purple indicates the devices are distant from each other. Further, in some embodiments, sound can be used. For example, a rapid beeping sound, fast tempo music, and/or high pitch tones can indicate the devices are proximate to each other and a slow beeping, slow temp music, and/or low pitch tones can indicate the devices are distant from each other. In some embodiments where the pairing motion sequence requires that the motions be performed at a rate faster than a mobility threshold, graphics, color, and/or sound can be used to indicate that the motions need to be performed faster. For example, if the user is moving the BGM 102 too slowly, the indicator bar 408 can flash red. If the rate exceeds the mobility threshold, the indicator bar can be displayed in a solid blue color.

Figure 5:
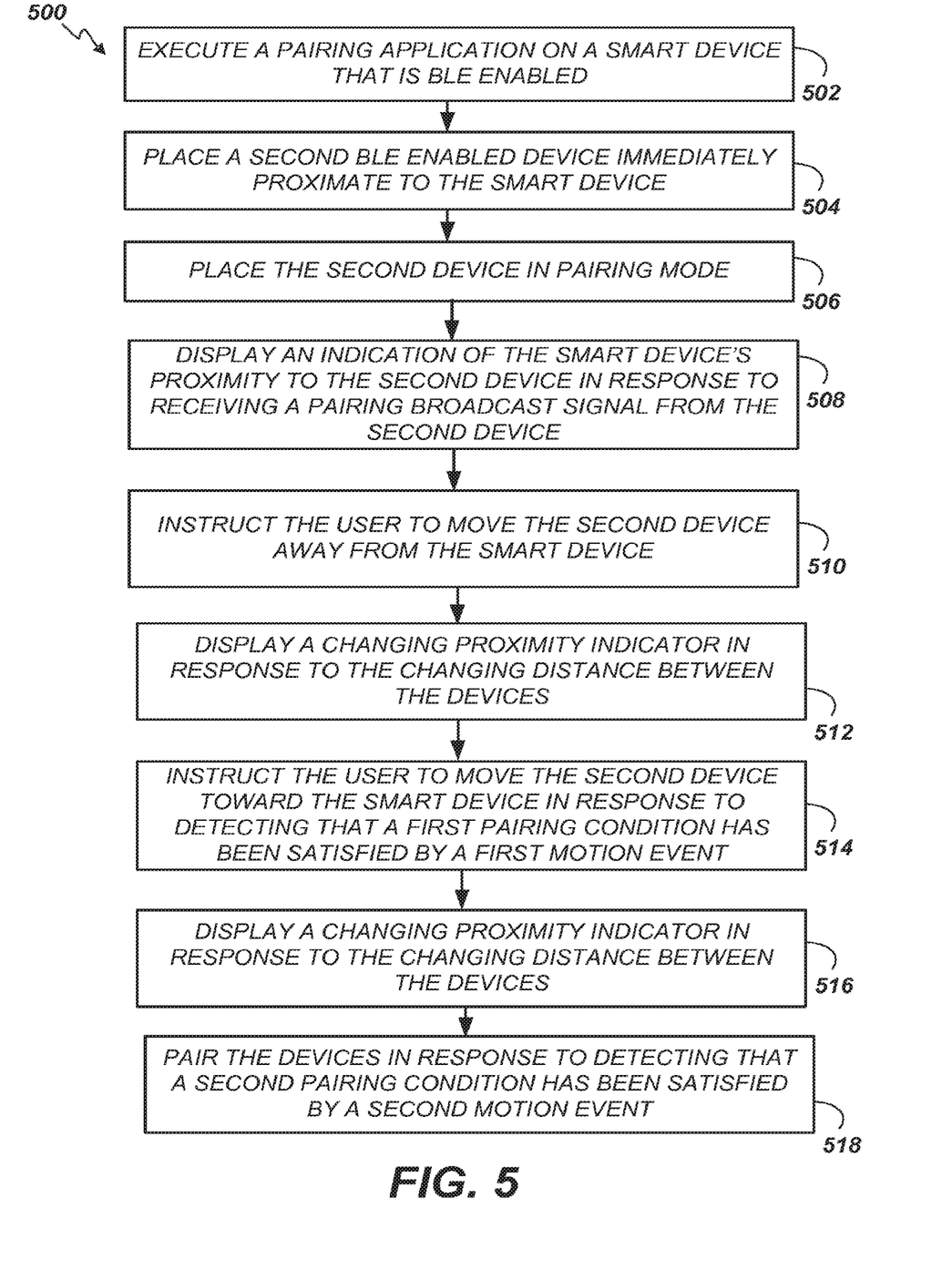
FIG. 5 depicts a flowchart illustrating an example method according to embodiments of the present invention.

Turning now to FIG. 5, a flow chart depicting an example method 500 of pairing wireless devices according to embodiments of the present invention is described. The method 500 starts with executing an application on a smart device (e.g., a smartphone, a tablet, a laptop computer, etc.) that is BLE enabled (502). While embodiments of the invention can use other wireless communication protocols, the example method 500 will be described using BLE to better illustrate the embodiment. The application can be a dedicated pairing application or it can be part of a larger application that will use the wireless connection established by pairing the device. The application can use/implement the embodiments of the logic circuits described above with respect to FIGS. 2 and 3 as well as the user interface embodiments described above with respect to FIG. 4. In some embodiments, the application will place the smart device in a pairing mode.

The second device, which is also BLE enabled, is placed immediately proximate to the smart device (504). The second device is then placed in pairing mode (506) The smart device displays an indication of its proximity to the second device in response to receiving the second device's pairing broadcast signal (508). The smart device instructs the user to move the second device away from the smart device (510). This motion represents a first motion pairing event that once completed, will satisfy a first pairing condition.

In response to the changing distance between the two devices, the smart device displays a changing proximity indicator (512). Once the smart device detects that the second device has been moved away a sufficient distance to satisfy a first predefined pairing motion sequence/event condition, the smart device instructs the user to move the second device toward the smart device (514). This motion represents a second motion pairing event that once completed, will satisfy a second pairing condition.

In response to the changing distance between the two devices, the smart device displays a changing proximity indicator (516). Once the smart device detects that the second device has been moved close enough to the smart device to satisfy a second predefined pairing motion sequence condition, the smart device pairs with the second device (518).

This example includes two pairing conditions that are satisfied at two different times but in a pre-defined sequence. As indicated above, the pairing conditions can require multiple motion events that can be required to be completed in parallel and/or in a sequential order.

Numerous embodiments are described in this disclosure, and are presented for illustrative purposes only. The described embodiments are not, and are not intended to be, limiting in any sense. The presently disclosed inventive concepts are widely applicable to numerous embodiments, as is readily apparent from the disclosure. One of ordinary skill in the art will recognize that the disclosed embodiments may be practiced with various modifications and alterations, such as structural, logical, software, and electrical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

The present disclosure is neither a literal description of all embodiments nor a listing of features of the invention that must be present in all embodiments.

The Title (set forth at the beginning of the first page of this disclosure) is not to be taken as limiting in any way as the scope of the disclosed invention(s).

The term "product" means any machine, manufacture and/or composition of matter as contemplated by 35 U.S.C. § 101, unless expressly specified otherwise.

The terms "an embodiment", "embodiment", "embodiments", "the embodiment", "the embodiments", "one or more embodiments", "some embodiments", "one embodiment" and the like mean "one or more (but not all) disclosed embodiments", unless expressly specified otherwise.

The terms "the invention" and "the present invention" and the like mean "one or more embodiments of the present invention."

A reference to "another embodiment" in describing an embodiment does not imply that the referenced embodiment is mutually exclusive with another embodiment (e.g., an embodiment described before the referenced embodiment), unless expressly specified otherwise.

The terms "including", "comprising" and variations thereof mean "including but not limited to", unless expressly specified otherwise.

The terms "a", "an" and "the" mean "one or more", unless expressly specified otherwise.

The term "and/or", when such term is used to modify a list of things or possibilities (such as an enumerated list of possibilities) means that any combination of one or more of the things or possibilities is intended, such that while in some embodiments any single one of the things or possibilities may be sufficient in other embodiments two or more (or even each of) the things or possibilities in the list may be preferred, unless expressly specified otherwise. Thus for example, a list of "a, band/or c" means that any of the following interpretations would be appropriate: (i) each of "a", "b" and "c"; (ii) "a" and "b"; (iii) "a" and "c"; (iv) "b" and "c"; (v) only "a"; (vi) only "b"; and (vii) only "c."

The term "plurality" means "two or more", unless expressly specified otherwise.

The term "herein" means "in the present disclosure, including anything which may be incorporated by reference", unless expressly specified otherwise.

The phrase "at least one of", when such phrase modifies a plurality of things (such as an enumerated list of things) means any combination of one or more of those things, unless expressly specified otherwise. For example, the phrase at least one of a widget, a car and a wheel means either (i) a widget, (ii) a car, (iii) a wheel, (iv) a widget and a car, (v) a widget and a wheel, (vi) a car and a wheel, or (vii) a widget, a car and a wheel.

The phrase "based on" does not mean "based only on", unless expressly specified otherwise. In other words, the phrase "based on" describes both "based only on" and "based at least on".

Each process (whether called a method, algorithm or otherwise) inherently includes one or more steps, and therefore all references to a "step" or "steps" of a process have an inherent antecedent basis in the mere recitation of the term "process" or a like term. Accordingly, any reference in a claim to a 'step' or 'steps' of a process has sufficient antecedent basis.

When an ordinal number (such as "first", "second", "third" and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget". Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

When a single device, component or article is described herein, more than one device, component or article (whether or not they cooperate) may alternatively be used in place of the single device, component or article that is described. Accordingly, the functionality that is described as being possessed by a device may alternatively be possessed by more than one device, component or article (whether or not they cooperate).

Similarly, where more than one device, component or article is described herein (whether or not they cooperate), a single device, component or article may alternatively be used in place of the more than one device, component or article that is described. For example, a plurality of computer-based devices may be substituted with a single computer-based device. Accordingly, the various functionality that is described as being possessed by more than one device, component or article may alternatively be possessed by a single device, component or article.

The functionality and/or the features of a single device that is described may be alternatively embodied by one or more other devices that are described but are not explicitly described as having such functionality and/or features. Thus, other embodiments need not include the described device itself, but rather can include the one or more other devices which would, in those other embodiments, have such functionality/features.

Devices that are in communication with each other need not be in continuous communication with each other, unless expressly specified otherwise. On the contrary, such devices need only transmit to each other as necessary or desirable, and may actually refrain from exchanging data most of the time. For example, a machine in communication with another machine via the Internet may not transmit data to the other machine for weeks at a time. In addition, devices that are in communication with each other may communicate directly or indirectly through one or more intermediaries.

A description of an embodiment with several components or features does not imply that all or even any of such components and/or features are required. On the contrary, a variety of optional components are described to illustrate the wide variety of possible embodiments of the present invention(s). Unless otherwise specified explicitly, no component and/or feature is essential or required.

Further, although process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

Although a process may be described as including a plurality of steps, that does not indicate that all or even any of the steps are essential or required. Various other embodiments within the scope of the described invention(s) include other processes that omit some or all of the described steps. Unless otherwise specified explicitly, no step is essential or required.

Although a product may be described as including a plurality of components, aspects, qualities, characteristics and/or features, that does not indicate that all of the plurality are essential or required. Various other embodiments within the scope of the described invention(s) include other products that omit some or all of the described plurality.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise. For example, the enumerated list "a computer, a laptop, a PDA" does not imply that any or all of the three items of that list are mutually exclusive and does not imply that any or all of the three items of that list are comprehensive of any category.

Headings of sections provided in this disclosure are for convenience only, and are not to be taken as limiting the disclosure in any way.

"Determining" something can be performed in a variety of manners and therefore the term "determining" (and like terms) includes calculating, computing, deriving, looking up (e.g., in a table, database or data structure), ascertaining, recognizing, and the like.

A "display" as that term is used herein is an area that conveys information to a viewer. The information may be dynamic, in which case, an LCD, LED, CRT, Digital Light Processing (DLP), rear projection, front projection, or the like may be used to form the display. The aspect ratio of the display may be 4:3, 16:9, or the like. Furthermore, the resolution of the display may be any appropriate resolution such as 480i, 480p, 720p, 1080i, 1080p or the like. The format of information sent to the display may be any appropriate format such as Standard Definition Television (SDTV), Enhanced Definition TV (EDTV), High Definition TV (HDTV), or the like. The information may likewise be static, in which case, painted glass may be used to form the display. Note that static information may be presented on a display capable of displaying dynamic information if desired. Some displays may be interactive and may include touch screen features or associated keypads as is well understood.

The present disclosure may refer to a "control system," interface, or program. A control system, interface, or program, as that term is used herein, may be a computer processor coupled with an operating system, device drivers, and appropriate programs (collectively "software") with instructions to provide the functionality described for the control system. The software is stored in an associated memory device (sometimes referred to as a computer readable medium). While it is contemplated that an appropriately programmed general purpose computer or computing device may be used, it is also contemplated that hard-wired circuitry or custom hardware (e.g., an application specific integrated circuit (ASIC)) may be used in place of, or in combination with, software instructions for implementation of the processes of various embodiments. Thus, embodiments are not limited to any specific combination of hardware and software.

A "processor" means any one or more microprocessors, Central Processing Unit (CPU) devices, computing devices, microcontrollers, digital signal processors, or like devices. Exemplary processors are the INTEL PENTIUM or AMD ATHLON processors.

The term "computer-readable medium" refers to any statutory medium that participates in providing data (e.g., instructions) that may be read by a computer, a processor or a like device. Such a medium may take many forms, including but not limited to non-volatile media, volatile media, and specific statutory types of transmission media. Non-volatile media include, for example, optical or magnetic disks and other persistent memory. Volatile media include DRAM, which typically constitutes the main memory. Statutory types of transmission media include coaxial cables, copper wire and fiber optics, including the wires that comprise a system bus coupled to the processor. Common forms of computer-readable media include, for example, a floppy disk, a flexible disk, hard disk, magnetic tape, any other magnetic medium, a CD-ROM, Digital Video Disc (DVD), any other optical medium, punch cards, paper tape, any other physical medium with patterns of holes, a RAM, a PROM, an EPROM, a FLASH-EEPROM, a USB memory stick, a dongle, any other memory chip or cartridge, a carrier wave, or any other medium from which a computer can read. The terms "computer-readable memory" and/or "tangible media" specifically exclude signals, waves, and wave forms or other intangible or non-transitory media that may nevertheless be readable by a computer.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols. For a more exhaustive list of protocols, the term "network" is defined below and includes many exemplary protocols that are also applicable here.

It will be readily apparent that the various methods and algorithms described herein may be implemented by a control system and/or the instructions of the software may be designed to carry out the processes of the present invention.

Where databases are described, it will be understood by one of ordinary skill in the art that (i) alternative database structures to those described may be readily employed, and (ii) other memory structures besides databases may be readily employed. Any illustrations or descriptions of any sample databases presented herein are illustrative arrangements for stored representations of information. Any number of other arrangements may be employed besides those suggested by, e.g., tables illustrated in drawings or elsewhere. Similarly, any illustrated entries of the databases represent exemplary information only; one of ordinary skill in the art will understand that the number and content of the entries can be different from those described herein. Further, despite any depiction of the databases as tables, other formats (including relational databases, object-based models, hierarchical electronic file structures, and/or distributed databases) could be used to store and manipulate the data types described herein. Likewise, object methods or behaviors of a database can be used to implement various processes, such as those described herein. In addition, the databases may, in a known manner, be stored locally or remotely from a device that accesses data in such a database. Furthermore, while unified databases may be contemplated, it is also possible that the databases may be distributed and/or duplicated amongst a variety of devices.

As used herein a "network" is an environment wherein one or more computing devices may communicate with one another. Such devices may communicate directly or indirectly, via a wired or wireless medium such as the Internet, LAN, WAN or Ethernet (or IEEE 802.3), Token Ring, or via any appropriate communications means or combination of communications means. Exemplary protocols include but are not limited to: Bluetooth™, Time Division Multiple Access (TDMA), Code Division Multiple Access (CDMA), Global System for Mobile communications (GSM), Enhanced Data rates for GSM Evolution (EDGE), General Packet Radio Service (GPRS), Wideband CDMA (WCDMA), Advanced Mobile Phone System (AMPS), Digital AMPS (D-AMPS), IEEE 802.11 (WI-FI), IEEE 802.3, SAP, the best of breed (BOB), system to system (S2S), or the like. Note that if video signals or large files are being sent over the network, a broadband network may be used to alleviate delays associated with the transfer of such large files, however, such is not strictly required. Each of the devices is adapted to communicate on such a communication means. Any number and type of machines may be in communication via the network. Where the network is the Internet, communications over the Internet may be through a website maintained by a computer on a remote server or over an online data network including commercial online service providers, bulletin board systems, and the like. In yet other embodiments, the devices may communicate with one another over RF, cable TV, satellite links, and the like. Where appropriate encryption or other security measures such as logins and passwords may be provided to protect proprietary or confidential information.

It will be readily apparent that the various methods and algorithms described herein may be implemented by, e.g., appropriately programmed general purpose computers and computing devices. Typically a processor (e.g., one or more microprocessors) will receive instructions from a memory or like device, and execute those instructions, thereby performing one or more processes defined by those instructions. Further, programs that implement such methods and algorithms may be stored and transmitted using a variety of media (e.g., computer readable media) in a number of manners. In some embodiments, hard-wired circuitry or custom hardware may be used in place of, or in combination with, software instructions for implementation of the processes of various embodiments. Thus, embodiments are not limited to any specific combination of hardware and software. Accordingly, a description of a process likewise describes at least one apparatus for performing the process, and likewise describes at least one computer-readable medium and/or memory for performing the process. The apparatus that performs the process can include components and devices (e.g., a processor, input and output devices) appropriate to perform the process. A computer-readable medium can store program elements appropriate to perform the method.

The present disclosure provides, to one of ordinary skill in the art, an enabling description of several embodiments and/or inventions. Some of these embodiments and/or inventions may not be claimed in the present application, but may nevertheless be claimed in one or more continuing applications that claim the benefit of priority of the present application. Applicants intend to file additional applications to pursue patents for subject matter that has been disclosed and enabled but not claimed in the present application.

The foregoing description discloses only example embodiments of the invention. Modifications of the above-disclosed apparatus, systems and methods which fall within the scope of the invention will be readily apparent to those of ordinary skill in the art.

Accordingly, while the present invention has been disclosed in connection with exemplary embodiments thereof, it should be understood that other embodiments may fall within the spirit and scope of the invention, as defined by the following claims.

The invention claimed is:

1. A smart device comprising:
one or more processors; and
one or more non-transitory computer-readable media storing instructions that, when executed by the one or more processors, perform a method for detecting a physical motion pairing event between the smart device and a second device, the method comprising:
receiving at least a first signal from a signal generator included in one or both of the smart device or the second device;
determining whether the first signal exceeds a threshold;
transmitting a second signal indicating whether or not the first signal exceeds the threshold; and
upon the first signal exceeding the threshold, indicating, via the second signal, that the physical motion pairing event between the smart device and a second device has occurred, the physical motion pairing event causing the smart device to establish a communications link with the second device.

2. The smart device of claim 1, wherein the first signal comprises accelerometer data, and wherein the threshold comprises a tap threshold, the tap threshold indicative of whether the smart device intentionally taps the second device.

3. The smart device of claim 2, further comprising:
filtering the accelerometer data to generate filtered accelerometer data; and
processing the filtered accelerometer data before determining whether the first signal exceeds the threshold.

4. The smart device of claim 1, wherein the signal generator comprises a radio receiver, the first signal being received from the radio receiver, wherein the threshold comprises one or more of a mobility threshold or a proximity threshold, and further comprising:
processing the first signal before determining whether the first signal exceeds the threshold.

5. The smart device of claim 1, further comprising:
following the physical motion pairing event, receiving information indicative of blood glucose data of a user as measured by the second device.

6. The smart device of claim 5, further comprising:
indicating, at the smart device, that the physical motion pairing event must occur to receive the information indicative of the blood glucose data of the user as measured by the second device.

7. The smart device of claim 1, further comprising a display configured to indicate to a user of the smart device the physical motion pairing event that needs to occur to pair the smart device with the second device.

8. A method for pairing a first device with a second device upon detection of a physical motion pairing event, the method comprising:
receiving at least one signal of a plurality of signals from a signal generator included in either the first device or the second device;

processing the at least one signal of the plurality of signals to generate at least one processed signal;

comparing the at least one processed signal to a predefined threshold value;

if the at least one signal is at or exceeds the predefined threshold value, identifying the physical motion pairing event between the first device and the second device; and pairing the first device with the second device if the physical motion pairing event is identified, wherein pairing the first device with the second device establishes a communications link between the first device and the second device.

9. The method of claim 8, wherein the first device comprises a blood glucose meter and the second device comprises a smart device.

10. The method of claim 9, wherein the second device includes a proximity indicator, the proximity indicator configured to indicate a proximity of the first device with the second device.

11. The method of claim 10, further comprising:
indicating, via the smart device, that the smart device is paired with the blood glucose meter.

12. The method of claim 8, wherein the predefined threshold value comprises at least one of a tap threshold, a mobility threshold, or a proximity threshold.

13. The method of claim 12, further comprising:
filtering the at least one signal; and
enhancing the at least one signal so as to accurately identify a tap event.

14. The method of claim 12, wherein the physical motion pairing event is identified if each of the tap threshold, the mobility threshold, and the proximity threshold are met or exceeded by the plurality of signals.

15. A motion detection system, comprising:
a first device including a radio receiver; and
a second device including an accelerometer, one or more processors, and one or more non-transitory computer-readable media storing instructions that, when executed by the one or more processors, perform a method for detecting a physical motion pairing event between the first device and the second device, the method comprising:
receiving at least one signal of a plurality of signals from the radio receiver or the accelerometer;
comparing the at least one signal to a threshold value; and
generating an output signal indicating if the at least one signal is at or exceeds the threshold value,
wherein if the at least one signal is at or exceeds the threshold value, the first device executes pairing with the second device such that a communications link is established between the first device and the second device.

16. The motion detection system of claim 15, wherein the second device further comprises a proximity indicator configured to indicate a proximity of the first device and the second device.

17. The motion detection system of claim 16, further comprising:
indicating, via the proximity indicator, once the proximity is within a predefined threshold proximity.

18. The motion detection system of claim 16, wherein the proximity is indicated via one or both of a display or a sound.

19. The motion detection system of claim 15, wherein the first device comprises a blood glucose meter and the second device comprises a smart device.

20. The motion detection system of claim 19, further comprising a third device configured to receive information indicative of blood glucose data from one or both of the blood glucose meter or the smart device following the physical motion pairing event.

* * * * *